US010254245B2

United States Patent
Knopfmacher et al.

(10) Patent No.: US 10,254,245 B2
(45) Date of Patent: Apr. 9, 2019

(54) DEVICES, SYSTEMS AND METHODS FOR DETECTING VIABLE INFECTIOUS AGENTS IN A FLUID SAMPLE USING AN ELECTROLYTE-INSULATOR-SEMICONDUCTOR SENSOR

(71) Applicant: Avails Medical, Inc., Palo Alto, CA (US)

(72) Inventors: Oren S. Knopfmacher, Palo Alto, CA (US); Meike Herget, Woodside, CA (US); Michael D. Laufer, Menlo Park, CA (US); August Estabrook, South San Francisco, CA (US)

(73) Assignee: Avails Medical, Inc., Menlo Park, CA (US)

( * ) Notice: Subject to any disclaimer, the term of this patent is extended or adjusted under 35 U.S.C. 154(b) by 298 days.

(21) Appl. No.: 15/412,934

(22) Filed: Jan. 23, 2017

(65) Prior Publication Data

US 2017/0212075 A1     Jul. 27, 2017

Related U.S. Application Data

(60) Provisional application No. 62/286,884, filed on Jan. 25, 2016.

(51) Int. Cl.
*G01N 1/00* (2006.01)
*G01N 27/416* (2006.01)
(Continued)

(52) U.S. Cl.
CPC ... *G01N 27/4166* (2013.01); *G01N 33/48714* (2013.01); *G01N 33/49* (2013.01); *G01N 27/227* (2013.01)

(58) Field of Classification Search
CPC .................................................. G01N 27/4166
See application file for complete search history.

(56) References Cited

U.S. PATENT DOCUMENTS

| 4,236,893 A | 12/1980 | Rice |
| 4,314,821 A | 2/1982 | Rice |

(Continued)

FOREIGN PATENT DOCUMENTS

| WO | WO 2003/044530 | 5/2003 |
| WO | WO 2007/035814 | 3/2007 |

(Continued)

OTHER PUBLICATIONS

Dortet, Laurent et al., "Bloodstream Infections Caused by *Pseudomonas* spp.: How to Detect Carbapenemase Producers Directly from Blood Cultures", Journal of Clinical Microbiology:, 52(4):1269-1273, Apr. 2014.

(Continued)

*Primary Examiner* — Jyoti Nagpaul
(74) *Attorney, Agent, or Firm* — Levine Bagade Han LLP

(57) ABSTRACT

Various devices, systems and methods for detecting a susceptibility of an infectious agent to an anti-infective are described herein. A method comprises introducing a fluid sample to a first surface and a second surface; exposing the first surface to a first solution; exposing, the second surface to a second solution, wherein the second surface comprises an anti-infective; sampling the first solution after exposing the first solution to the first surface; sampling the second solution after exposing the second solution to the second surface; monitoring a first electrical characteristic of a first electrolyte-insulator-semiconductor (EIS) sensor exposed to the first solution sampled; monitoring a second electrical characteristic of a second EIS sensor exposed to the second solution sampled; and comparing the first electrical characteristic and the second electrical characteristic to assess the susceptibility of the infectious agent to the anti-infective.

20 Claims, 6 Drawing Sheets

(51) Int. Cl.
*G01N 33/487* (2006.01)
*G01N 33/49* (2006.01)
*G01N 27/22* (2006.01)

(56) References Cited

U.S. PATENT DOCUMENTS

| | | | |
|---|---|---|---|
| 4,448,534 | A | 5/1984 | Wertz et al. |
| 4,735,906 | A | 4/1988 | Bastiaans |
| 4,767,719 | A | 8/1988 | Finlan |
| 4,789,804 | A | 12/1988 | Karube et al. |
| 4,822,566 | A | 4/1989 | Newman |
| 4,965,193 | A | 10/1990 | Chen |
| 4,977,247 | A | 12/1990 | Fahnestock et al. |
| 5,064,756 | A | 11/1991 | Carr et al. |
| 5,077,210 | A | 12/1991 | Eigler et al. |
| 5,111,221 | A | 5/1992 | Fare et al. |
| 5,182,005 | A | 1/1993 | Schwiegk et al. |
| 5,447,845 | A | 9/1995 | Chu et al. |
| 5,821,399 | A | 10/1998 | Zelin |
| 5,922,537 | A | 7/1999 | Ewart et al. |
| 6,280,586 | B1 | 8/2001 | Wolf et al. |
| 6,368,795 | B1 | 4/2002 | Hefti |
| 6,391,558 | B1 | 5/2002 | Henkens et al. |
| 6,548,263 | B1 | 4/2003 | Kapur et al. |
| 6,548,311 | B1 | 4/2003 | Knoll |
| 6,780,307 | B2 | 8/2004 | Kidwell |
| 8,508,100 | B2 | 8/2013 | Lee et al. |
| 8,728,844 | B1 | 5/2014 | Liu et al. |
| 9,377,456 | B1 | 6/2016 | Herget et al. |
| 9,702,847 | B2 | 7/2017 | Herget et al. |
| 9,766,201 | B2 | 9/2017 | Herget et al. |
| 2002/0127623 | A1 | 9/2002 | Minshull et al. |
| 2003/0073071 | A1 | 4/2003 | Fritz et al. |
| 2003/0109056 | A1 | 6/2003 | Vossmeyer et al. |
| 2003/0119208 | A1 | 6/2003 | Yoon et al. |
| 2006/0102935 | A1 | 5/2006 | Yitzchaik et al. |
| 2006/0197118 | A1 | 9/2006 | Migliorato et al. |
| 2006/0246426 | A1 | 11/2006 | Woodbury et al. |
| 2006/0286548 | A1 | 12/2006 | Liposky |
| 2007/0072187 | A1 | 3/2007 | Blok et al. |
| 2008/0012007 | A1 | 1/2008 | Li et al. |
| 2008/0199863 | A1 | 8/2008 | Haake et al. |
| 2009/0008247 | A1 | 1/2009 | Chen et al. |
| 2009/0020438 | A1 | 1/2009 | Hodges |
| 2009/0273354 | A1 | 11/2009 | Dhirani et al. |
| 2010/0025660 | A1 | 2/2010 | Jain et al. |
| 2011/0306032 | A1 | 12/2011 | Galiano et al. |
| 2012/0032235 | A1 | 2/2012 | Bikumandla |
| 2012/0077692 | A1 | 3/2012 | Hassibi et al. |
| 2012/0088682 | A1 | 4/2012 | Rothberg et al. |
| 2012/0143027 | A1 | 6/2012 | Phillips et al. |
| 2012/0153262 | A1 | 6/2012 | Paranjape et al. |
| 2012/0153407 | A1 | 6/2012 | Chang et al. |
| 2012/0168306 | A1 | 7/2012 | Hassibi et al. |
| 2012/0208291 | A1 | 8/2012 | Wayne et al. |
| 2012/0261274 | A1 | 10/2012 | Rearick et al. |
| 2012/0279859 | A1 | 11/2012 | Rothberg et al. |
| 2013/0089883 | A1 | 4/2013 | Dallenne et al. |
| 2013/0089932 | A1 | 4/2013 | Wu et al. |
| 2013/0096013 | A1 | 4/2013 | Esfandyarpour et al. |
| 2013/0105868 | A1 | 5/2013 | Kalnitsky et al. |
| 2014/0057339 | A1 | 2/2014 | Esfandyarpour et al. |
| 2014/0134656 | A1 | 5/2014 | Dortet et al. |
| 2014/0191294 | A1 | 7/2014 | Bikumandla et al. |
| 2014/0231256 | A1 | 8/2014 | Packingham et al. |
| 2014/0349005 | A1 | 11/2014 | Everett et al. |
| 2015/0355129 | A1 | 12/2015 | Knopfmacher |
| 2016/0187332 | A1 | 6/2016 | Herget et al. |
| 2016/0187334 | A1 | 6/2016 | Herget et al. |
| 2016/0209356 | A1 | 7/2016 | Herget et al. |
| 2016/0266102 | A1 | 9/2016 | Knopfmacher |
| 2017/0058313 | A1 | 3/2017 | Knopfmacher et al. |
| 2017/0059508 | A1 | 3/2017 | Knopfmacher et al. |
| 2017/0336348 | A1 | 11/2017 | Herget et al. |
| 2017/0342459 | A1 | 11/2017 | Knopfmacher et al. |

FOREIGN PATENT DOCUMENTS

| | | |
|---|---|---|
| WO | WO 2010/062001 | 6/2010 |
| WO | WO 2012/078340 | 6/2012 |
| WO | WO 2013/096404 | 6/2013 |
| WO | WO 2014/134431 | 9/2014 |
| WO | WO 2015/077632 | 5/2015 |
| WO | WO 2015/188002 | 12/2015 |
| WO | WO 2016/061453 | 4/2016 |
| WO | WO 2016/109569 | 7/2016 |
| WO | WO 2017/132095 | 8/2017 |
| WO | WO 2017/209839 | 12/2017 |

OTHER PUBLICATIONS

Dortet, Laurent et al., "CarbAcineto NP Test for Rapid Detection of Carbapenemase-Producing *Acinetobacter* spp.", Journal of Clinical Microbiology, 52(7):2359-2364, Jul. 2014.

Dortet, Laurent et al., "Evaluation of the RAPIDECw CARBA NP, the Rapid CARB Screenw and the Carba NP test for biochemical detection of carbapenemase-producing Enterobacteriaceae", J Antimicrob Chemother, 70:3014-3022, 2015.

Dortet, Laurent et al., "Further Proofs of Concept for the Carba NP Test", Antimicrobial Agents and Chemotherapy, 58(2):1269, Feb. 2014.

Dortet, Laurent et al., "Rapid Identification of Carbapenemase Types in *Enterobacteriaceae* and *Pseudomonas* spp. by Using a Biochemical Test", Antimicrobial Agents and Chemotherapy, 56(12):6437-6440, Dec. 2012.

Estrela, Pedro et al., "Label-Free Sub-picomolar Protein Detection with Field-Effect Transistors," Analytical Chemistry, vol. 82, No. 9, May 1, 2010, 3531-3536.

Hammock, Mallory L. et al., "Electronic readout ELISA with organic field-effect transistors as a prognostic test for preeclampsia," Advanced Materials, 26: 6138-6144. doi: 10.1002/adma.201401829.

Kumar et al., "Sensitivity Enhancement Mechanisms in Textured Dielectric Based Electrolyte-Insulator-Semiconductor (EIS) Sensors," *ECS Journal of Solid State Science and Technology*, 4(3):N18-N23 (2015).

Mathias, W. et al., "Selective Sodium Sensing with Gold-Coated Silicon Nanowire Field-Effect Transistors in a Differential Setup," ACS Nano 7, 5978-5983 (2013).

Nordmann, Patrice et al., "Strategies for identification of carbapenemase-producing Enterobacteriaceae", J Antimicrob Chemother, 68:487-489, 2013.

Poghossian et al., "Penicillin Detection by Means of Field-Effect Based Sensors: EnFET, Capacitive EIS Sensor or LAPS?", *Sensors and Actuators B*, 78:237 (2001).

Poirel, Laurent et al., "Rapider Carba NP Test for Rapid Detection of Carbapenemase Producers", Journal of Clinical Microbiology, 53(9):3003-3008, Sep. 2015.

Salm, Eric et al., "Electrical Detection of Nucleic Acid Amplification Using an On-Chip Quasi-Reference Electrode and a PVC REFET," dx.doi.org/10.1021/ac500897t, *Anal. Chem.*, 2014, 86, 6968-6975.

Schoning, Michael J., "'Playing Around' with Field-Effect Sensors on the Basis of EIS Structures, LAPS and ISFETs." *Sensors*, 5:126-138 (2005).

U.S. Appl. No. 14/297,603, filed Jun. 5, 2014.
U.S. Appl. No. 14/586,802, filed Dec. 30, 2014.
U.S. Appl. No. 14/599,190, filed Jan. 16, 2015.
U.S. Appl. No. 15/081,491, filed Mar. 25, 2016.
U.S. Appl. No. 15/159,625, filed May 19, 2016.
U.S. Appl. No. 14/878,936, filed Oct. 8, 2015.
U.S. Appl. No. 15/236,260, filed Aug. 12, 2016.
U.S. Appl. No. 15/482,307, filed Apr. 7, 2017.
U.S. Appl. No. 15/670,579, filed Aug. 7, 2017.

DEVICES, SYSTEMS AND METHODS FOR DETECTING VIABLE INFECTIOUS AGENTS IN A FLUID SAMPLE USING AN ELECTROLYTE-INSULATOR-SEMICONDUCTOR SENSOR

CROSS-REFERENCE TO RELATED APPLICATION

This application claims the benefit of U.S. Provisional Application No. 62/286,884 filed on Jan. 25, 2016, which is hereby incorporated by reference in its entirety.

TECHNICAL FIELD

The present disclosure relates generally to in vitro detection of infectious agents and, more specifically, to devices, systems, and methods for detecting viable infectious agents in a fluid sample using an electrolyte-insulator-semiconductor (EIS) sensor.

BACKGROUND

Infections caused by anti-infective resistant infectious agents or microbes are a significant problem for healthcare professionals in hospitals, nursing homes, and other healthcare environments. For example, such infections can lead to a potentially life-threatening complication known as sepsis where chemicals released into the bloodstream by an infectious agent can trigger a dangerous whole-body inflammatory response as well as a vasoactive response causing fever, low blood pressure, and possibly death. When faced with such an infection, a preferred course of action is for a clinician to use anti-infective compounds judiciously, preferably only those necessary to alleviate the infection. However, what occurs most frequently today is that until the organism is identified and tested for drug sensitivity, broad spectrum anti-infectives, often multiple drugs, are given to the patient to insure adequacy of treatment. This tends to result in multiple drug resistant infectious agents. Ideally, the sensitivity of the infectious agent would be detected soon after its presence is identified. The present disclosure presents devices, systems, and methods for accomplishing this goal.

Existing methods and instruments used to detect anti-infective resistance in infectious agents include costly and labor intensive microbial culturing techniques to isolate the infectious agent and include tests such as agar disk diffusion or broth microdilution where anti-infectives are introduced as liquid suspensions, paper disks, or dried gradients on agar media. However, those methods require manual interpretation by skilled personnel and are prone to technical or clinician error.

While automated inspection of such panels or media can reduce the likelihood of clinician error, current instruments used to conduct these inspections are often costly and require constant maintenance. In addition, current instruments often rely on an optical read-out of the investigated samples requiring bulky detection equipment and access to power supplies. Most importantly, these methods require days to obtain a result, as the infectious agents must reproduce several times in different media prior to being exposed to the anti-infective to determine their susceptibility.

In addition, such methods and instruments often cannot conduct such tests directly on a patient's bodily fluids and require lengthy sample preparation times.

As a result of the above limitations and restrictions, there is a need for improved devices, systems, and methods to quickly and effectively detect anti-infective resistant infectious agents in a patient sample.

SUMMARY

Various devices, systems and methods for detecting the susceptibility of an infectious agent in a patient sample to one or more anti-infectives are described herein.

In one embodiment, a method for detecting the susceptibility of an infectious agent to one or more anti-infectives can include introducing a fluid sample to a first surface and a second surface, exposing the first surface to a first solution, and exposing the second surface to a second solution. The second surface can comprise an anti-infective.

In some instances, the fluid sample can comprise the infectious agent and the infectious agent can be introduced to the first surface or the second surface through the fluid sample. The method can also include determining the presence of the infectious agent in the fluid sample.

The method can include sampling the first solution after exposing the first solution to the first surface. The method can also include sampling the second solution after exposing the second solution to the second surface. The method can include monitoring a first electrical characteristic of a first electrolyte-insulator-semiconductor (EIS) sensor exposed to the first solution sampled. The method can include monitoring a second electrical characteristic of a second EIS sensor exposed to the second solution sampled. The first electrical characteristic and/or the second electrical characteristic can be an electrical impedance, a voltage shift, a capacitance change, or a characteristic that is affected by a change in capacitance such as a change in resonant frequency (e.g., sound).

The method can further include comparing the first electrical characteristic and the second electrical characteristic to assess the susceptibility of the infectious agent to the anti-infective. Comparing the first electrical characteristic and the second electrical characteristic can include determining a difference between the first electrical characteristic and the second electrical characteristic. The difference between the first electrical characteristic and the second electrical characteristic can be a result of a difference in a solution characteristic of the first solution and the second solution. The difference in the solution characteristic of the first solution and the second solution can result from a difference in a molecular count, a concentration of an ion, and/or a solution temperature.

The first surface can be a filter surface or a well surface. The second surface can be separate from the first surface and can be another instance of the filter surface or the well surface. At least one of the first surface and the second surface can be a non-clogging filter. In addition, at least one of the first surface and the second surface can comprise pores of sequentially smaller pore size.

The infectious agent can be, but is not limited to, a bacteria, a fungus, a virus, or a priori. The first EIS sensor and the second EIS sensor can be housed by a protective chamber and the protective chamber can be an electrically isolated environment a temperature controlled chamber, and/or a light controlled chamber. The first solution can be directed to the first surface by a pump. The second solution can also be directed to the second surface by a pump.

In another embodiment, a method for detecting a susceptibility of an infectious agent to an anti-infective can include introducing a fluid sample to a first surface and a second surface, exposing the first surface to a first solution, and exposing the second surface to a second solution. The second surface can comprise an anti-infective.

In some instances, the fluid sample can comprise the infectious agent and the infectious agent can be introduced to the first surface or the second surface through the fluid sample. The method can also include determining the presence of the infectious agent in the fluid sample.

The method can include sampling the first solution after exposing the first solution to the first surface. The method can also include sampling the second solution after exposing the second solution to the second surface. The method can include monitoring a first electrical characteristic of an EIS sensor exposed to the first solution sampled. The method can also include monitoring a second electrical characteristic of the EIS sensor exposed to the second solution sampled.

The method can further include comparing the first electrical characteristic and the second electrical characteristic to assess the susceptibility of the infectious agent to the anti-infective. Comparing the first electrical characteristic and the second electrical characteristic can include determining a difference between the first electrical characteristic and the second electrical characteristic. The difference between the first electrical characteristic and the second electrical characteristic can be a result of a difference in a solution characteristic of the first solution and the second solution. The difference in the solution characteristic of the first solution and the second solution can result from a difference in a molecular count, a concentration of an ion, and/or a solution temperature.

The first surface can be a filter surface or a well surface. The second surface can be separate from the first surface and can be another instance of the filter surface or the well surface. At least one of the first surface and the second surface can be a non-clogging filter. In addition, at least one of the first surface and the second surface can comprise pores of sequentially smaller pore size.

The infectious agent can be, but is not limited to, a bacteria, a fungus, a virus, or a prion. The first sensor and the second sensor can be housed by a protective chamber and the protective chamber can be an electrically isolated environment, a temperature controlled chamber, and/or a light controlled chamber. The first solution can be directed to the first surface by a pump. The second solution can also be directed to the second surface by a pump.

BRIEF DESCRIPTION OF THE DR WINGS

DETAILED DESCRIPTION

Variations of the devices, systems, and methods described herein are best understood from the detailed description when read in conjunction with the accompanying drawings. It is emphasized that, according to common practice, the various features of the drawings may not be to scale. On the contrary, the dimensions of the various features may be arbitrarily expanded or reduced for clarity and not all features may be visible or labeled in every drawing. The drawings are taken for illustrative purposes only and are not intended to define or limit the scope of the claims to that which is shown.

Figure 1:
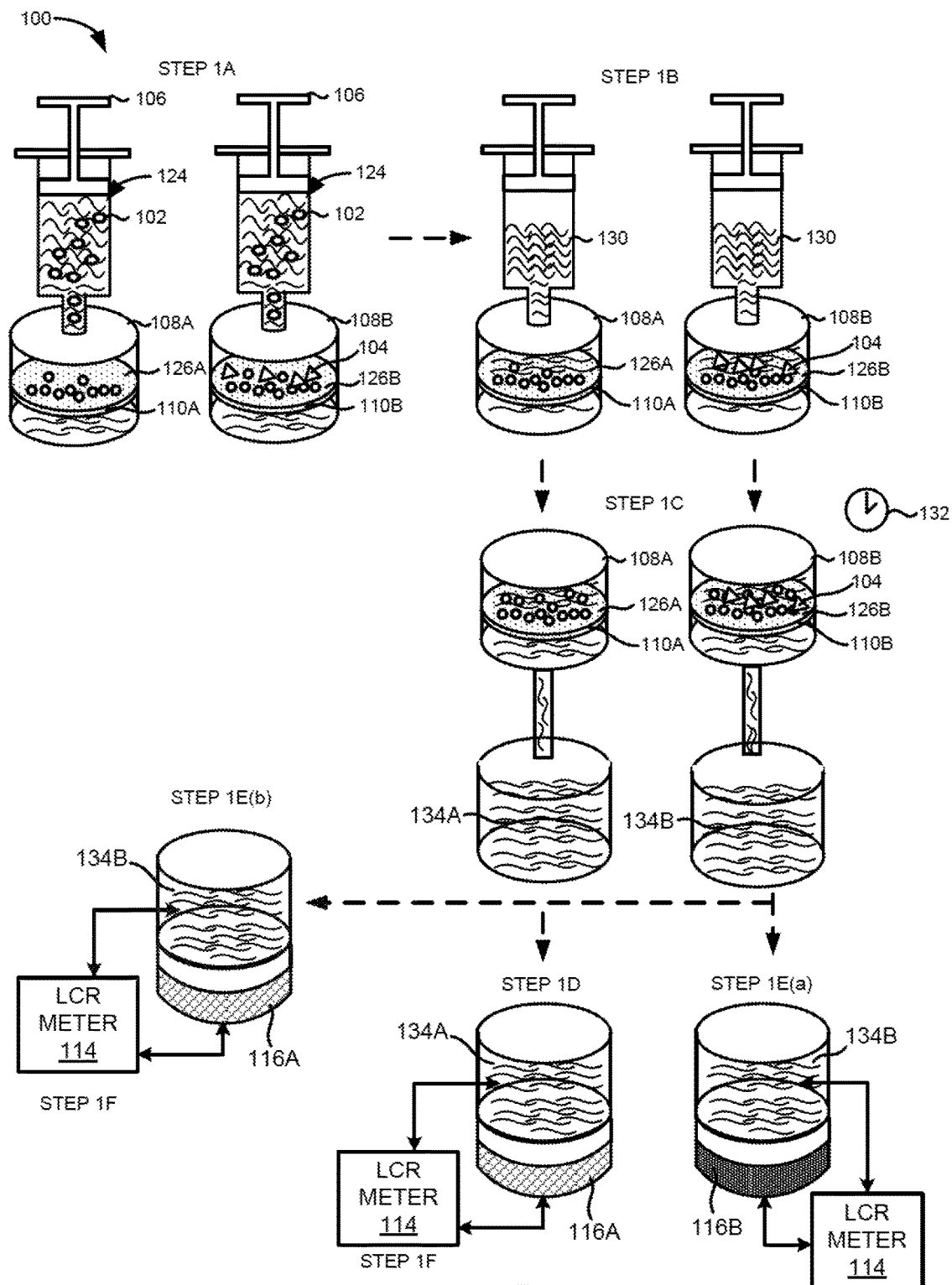
FIG. 1 illustrates one embodiment of a system for detecting a susceptibility of an infectious agent to one of more anti-infectives.

FIG. 1 illustrates an embodiment of a system 100 for detecting or assessing a. susceptibility of an infectious agent 102 to an anti-infective 104. The infectious agent 102 can be a bacteria, a fungus, a virus, or a priori.

In one embodiment, the system 100 can comprise a fluid delivery device 106, a first filter housing 108A containing a first filter 110A, a second filter housing 108B containing a second filter 110B, a first electrolyte-insulator-semiconductor (EIS) sensor 116A, a second EIS sensor 116B, and a parameter analyzer 114. The EIS sensors will be discussed in more detail in the sections that follow.

Figure 2A:
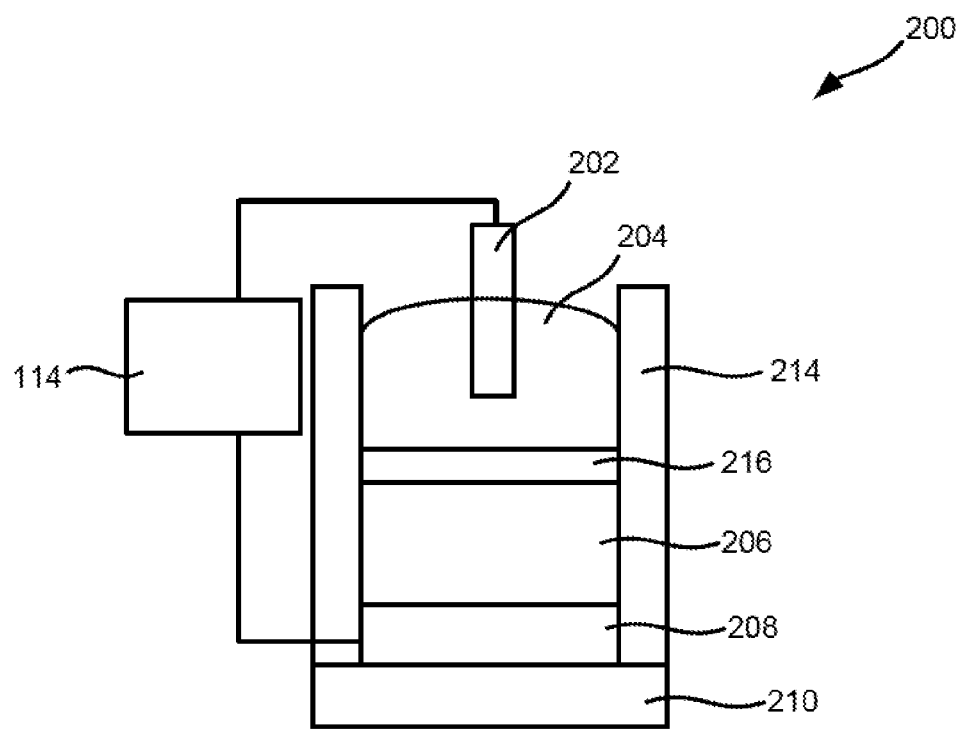
FIG. 2A illustrates a side view of an embodiment of an EIS sensor structure having an external reference electrode.
Figure 2B:
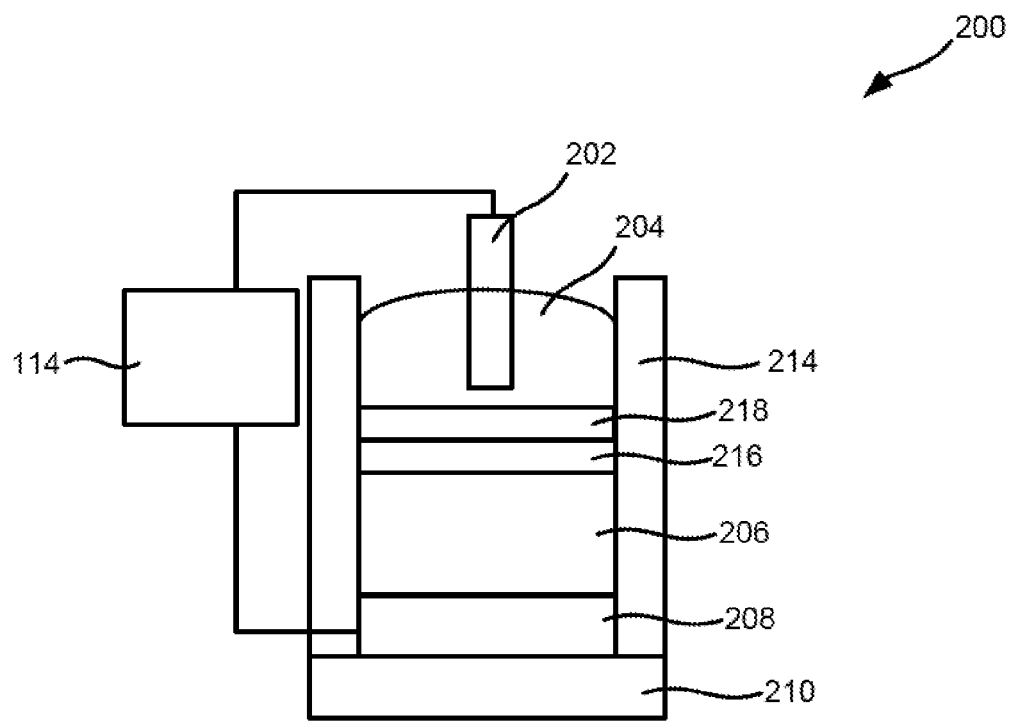
FIG. 2B illustrates a side view of an embodiment of an EIS sensor having an external reference electrode and a functionalization layer.

The first EIS sensor 116A, the second EIS sensor 116B, or a combination thereof can be located on a substrate 210 (see FIG. 2A or FIG. 2B). The substrate 112 can be comprised of a polymer or polymeric material, a metal, a ceramic, a semiconductor layer, an oxide layer, an insulator, or a combination thereof. Although not shown in FIG. 1, the parameter analyzer 114 can be integrated into one device with the first EIS sensor 116A, the second EIS sensor 116B, or a combination thereof. In other embodiments, the parameter analyzer 114 can be a standalone unit or device coupled to the substrate 202 and/or a reference electrode.

In another embodiment, the system 100 can comprise the fluid delivery device 106, the first filter housing 108A containing the first filter 110A, the second filter housing 108B containing the second filter 110B, one EIS sensor 116A (shown in step 1D and step 1E(b) of FIG. 1), and a parameter analyzer 114.

The system 100 can detect or assess the level of susceptibility of the infectious agent 102 to an anti-infective 104. In some instances, the fluid sample 124 can comprise the infectious agent 102. The fluid sample 124 can include a bodily fluid such as blood, serum, plasma, urine, saliva, joint fluid, semen, wound material, spinal fluid, mucus, or a combination thereof. In other embodiments, the fluid sample 124 can also include an environmental fluid such as liquids sampled from a stream, river, lake, ocean, contamination site, quarantine zone, or emergency area. The fluid sample 124 can also be a food sample.

The system 100 can also initially be used to determine the presence of the infectious agent 102 in the fluid sample 124 before detecting or assessing the level of susceptibility of the infectious agent 102 to the anti-infective 104.

The infectious agent 102 can be any metabolizing single or multi-cellular organism including a bacteria or fungus. The infectious agent 102 can also be a virus or a prion.

In certain embodiments, the infectious agent 102 can be a bacteria selected from the genera consisting of *Acinetobacter, Aeromonas, Bacillus Bacteroides, Citrobacter, Enterobacter, Escherichia, Klebsiella, Morganella, Pando-*

*raea, Proteus, Providencia, Pseudomonas, Ralstonia, Raoultella, Salmonella, Serratia, Shewanella, Shigella, Stenotrophomonas, Streptomyces, Staphylococcus, Enterococcus, Clostridium* or any combination thereof. In other embodiments, the infectious agent 102 can be a fungus selected from the genera consisting of *Candida, Cryptococcus*, or any combination thereof. In another embodiment, the infectious agent 102 can include amoeba. In further embodiments, the infectious agent 102 can be cancer cells and the anti-infectives 104 can be chemotherapeutics or other cancer treatments.

As illustrated in FIG. 1, the fluid delivery device 106 can deliver or inject the fluid sample 124 into the first filter housing 108A and the second filter housing 108B in step 1A. The fluid delivery device 106 can be a pump. For example, the fluid delivery device 106 can be a hydraulic pump, a pneumatic pump, a syringe pump, or a combination thereof. In other embodiments, the fluid delivery device 106 can be an injection cartridge, a microfluidic channel, a pipette, a reaction tube, a capillary, a test tube, a combination thereof, or a portion therein.

The first filter housing 108A or the second filter housing 108B can be a container or vessel configured to secure or enclose the first filter 110A or the second filter 110B, respectively. For example, the first filter housing 108A or the second filter housing 108B can be a protective chamber. The protective chamber can be an electrically isolated environment. The protective chamber can also be a temperature controlled chamber, a light controlled chamber, or a combination thereof.

The first filter 110A, the second filter 110B, or a combination thereof can be a non-clogging filter. The first filter surface 126A can be a non-clogging filter surface. The second filter surface 126B can also be a non-clogging filter surface. The first filter 110A, the second filter 110B, or a combination thereof can also have filter pores of sequentially smaller pore size. For example, the first filter 110A, the second filter 110B, or a combination thereof can have larger filter pores at the top of the filter and progressively smaller filters pores toward the bottom of the filter. Although not shown in FIG. 1, it is contemplated by this disclosure that the first filter 110A or the second filter 110B can refer to a plurality of filters in a stacked arrangement.

The first filter 110A can comprise the infectious agent 102 when the fluid sample 124 introduced to the first filter 110A comprises or carries the infectious agent 102. The second filter 110B can also comprise the infectious agent 102 when the fluid sample 124 introduced to the second filter 110B comprises or carries the infectious agent 102.

The first filter 110A can be a mesh or matrix structure for isolating or separating the infectious agent 102 or other molecules or cells from the supernatant of the fluid sample 124. The second filter 110B can also be a mesh or matrix structure for isolating or separating the infectious agent 102 or other molecules or cells from the supernatant of the fluid sample 124. In certain embodiments, the first filter 110A or the second filter 110B can be selected from the group consisting. of cellulose acetate, regenerated cellulose, nylon, polystyrene, polyvinylidene fluoride (PVDF), polyethersulfone (PES), polytetrafluorethylene (PTFE), glass microfiber, or a combination thereof.

The first filter 110A can comprise a first filter surface 126A. The first filter surface 126A can be the portion of the first filter 110A used to isolate or trap the infectious agent 102. The first filter surface 126A can include an external surface, an internal surface extending into the first filter 110A, or a combination thereof.

The second filter 110B can comprise a second filter surface 126B. The second filter surface 126B can be the portion of the second filter 110B used to isolate or trap the infectious agent 102. The second filter surface 126B can include an external surface, an internal surface extending into the second filter 110B, or a combination thereof.

The second filter 110B or the second filter surface 126B can comprise the anti-infective 104. The anti-infective 104 can be added or introduced to the second filter surface 126B before or after exposing the second filter surface 126B to the fluid sample 124.

In another embodiment, the anti-infective 104 can be incorporated or embedded into or coated onto the second filter 108B or the second filter surface 126B before exposing the second filter 110B or the second filter surface 126B to the fluid sample 124.

In yet another embodiment, the anti-infective 104 can be introduced through a solution exposed to the first filter 110A, the second filter 110B, or a combination thereof. For example, the anti-infective 104 can be introduced through the nutrient solution 130.

The anti-infective 104 can comprise a bacteriostatic anti-infective, a bactericidal anti-infective, an anti-fungal anti-infective, an antiviral anti-infective, a prion inhibitor, or a combination thereof.

In another embodiment, the anti-infective 104 can be a bacterial growth inhibitor or stimulator. The bacterial growth inhibitor or stimulator can selectively inhibit or promote the growth of gram positive or gram negative bacteria. The bacterial growth inhibitor or stimulator can comprise of dye or a chemical compound. In some embodiments, the dye can include, but is not limited to, Methylene blue, Bromothymol blue, Eosin B, Safranin O, Crystal violet, or a combination thereof. The chemical compound can include, but is not limited to, sodium azide, bile acids, high sodium chloride, or a combination thereof. The anti-infective 104 can also comprise a carbon source other than glucose, such as lactose or mannose, to select for certain bacterial species. The bacterial growth inhibitor, the carbon source, or a combination thereof can also be added to the nutrient solution 130.

The first filter housing 108A or the second filter housing 108B can have at least one opening which allows fluid or supernatant from the fluid sample 124 to evacuate the first filter housing 108A or the second filter housing 108B. For example, step 1A can include the additional step of discarding the fluid or supernatant from the fluid sample 124 through the opening after isolating the infectious agent 102 on the first filter surface 126A or the second filter surface 126B.

In an alternative embodiment not shown in FIG. 1, a stimulus solution can be added to the fluid sample 124 before introducing the fluid sample 124 to the first filter 110A or the second filter 110B. The stimulus solution can be a nutrient or growth solution. The stimulus solution can have a different composition than nutrient solution 130. The stimulus solution can be a super nutrient solution.

The fluid sample 124 can also be pre-filtered in a step before step 1A. This pre-filtering step can involve filtering the fluid sample 124 using a filter, a microfluidic filter, or a combination thereof to filter out other larger cellular components including blood cells or epithelial cells from the fluid sample 124 when the fluid sample 124 is composed of bodily fluid.

The same fluid delivery device 106 or another fluid delivery device 106 can also be used to deliver or inject nutrient solution 130 to the first filter housing 108A the second filter housing 108B, or a combination thereof in step 1B. The fluid delivery device 106 can continuously or periodically expose the first filter surface 126A, the second filter surface 126B, or a combination thereof to the nutrient solution 130.

After exposing the first filter 110A or the second filter 110B to the nutrient solution 130, the first filter 110A. or the second filter 110B can be heated to a temperature of between 30° C. and 40° C. and allowed to incubate for an incubation period 132 in step 1C. In one embodiment, the first filter 110A or the second filter 110B can be incubated while in the first filter housing 108A or the second filter housing 108B, respectively. In another embodiment, the first filter 110A or the second filter 110B can be removed from the first filter housing 108A or the second filter housing 10813, respectively, prior to incubation. In some embodiments, the first filter 110A, the second filter 110B, or a combination thereof can be incubated with the nutrient solution 130. The incubation period 132 can range from 15 minutes to over one hour. In other embodiments, the incubation period 132 can be less than 15 minutes. The incubation period 132 can be adjusted based on the type of infectious agent 102, such as the type of bacteria, fungus, virus, or prion.

The incubation period 132 can also be adjusted based on the amount of the infectious agent 102 present in the fluid sample 124. For example, the incubation period 132 can be increased when the amount of the infectious agent 102 is below a threshold amount. The first filter 110A or the second filter 110B can be allowed to incubate with the nutrient solution 130 in order to promote the proliferation of the infectious agent 102 on the first filter surface 126A or the second filter surface 126B, respectively. One advantage of incubating the first filter 110A and the second filter 110B is to increase the sensitivity of the system 100 to small amounts of the infectious agent 102. For example, incubating the first filter 110A and the second filter 110B can allow the system 100 to reduce its level of detection.

After incubating the first filter 110A or the second filter 110B, the effluent or outflow of the nutrient solution 130 exposed to the first filter 110A or the second filter 110B can be sampled. The effluent or outflow of the nutrient solution 130 exposed to the first filter 110A can be referred to as the first sample effluent 134A.

The first sample effluent 134A can be analyzed by a first EIS sensor 116A in step 1D. The first sample effluent 134A can be analyzed by applying or introducing an aliquot of the first sample effluent 134A to the first EIS sensor 116A. In another embodiment, the first sample effluent 134A can be analyzed by inserting a portion of the first EIS sensor 116A directly into the first sample effluent 134A.

The effluent or outflow of the nutrient solution 130 exposed to the second filter 110B can be referred to as the second sample effluent 134B. In one embodiment, the second sample effluent 134B can be analyzed by a second EIS sensor 116B in step 1E(a). The second sample effluent 134B can be analyzed by applying or introducing an aliquot of the second sample effluent 134B to the second EIS sensor 116B. In another embodiment, the second sample effluent 134B can be analyzed by inserting a portion of the second EIS sensor 116B directly into the second sample effluent 134B.

The first sample effluent 134A and the second sample effluent 134B can each comprise a solution characteristic 136. The solution characteristic 136 can refer to one or more attributes of the solution making up the first sample effluent 134A, the second sample effluent 134B, or a combination thereof. For example, the solution characteristic 136 can include a concentration of a solute, an absolute number or molecular count of solutes in solution, a solution temperature, or a combination thereof. For example, the solution characteristic 136 can refer to the amount or concentration of ions, organic molecules such as amino acids, vitamins or glucose, minerals, or other inorganic compounds in the sample effluent 134.

The solution characteristic 136 can vary as a result of natural changes due to the energy use, growth, and metabolism of the infectious agent 102. For example, the solution characteristic 136 can be a direct or indirect byproduct of a cellular activity undertaken by the infectious agent 102 such as cell metabolism or cell growth. The solution characteristic 136 can vary as a result of ions, organic molecules, or minerals produced by, consumed by, or otherwise attributed to the infectious agent 102 on the first filter surface 126A, the second filter surface 126B, or a combination thereof. For example, the solution characteristic 136 can change as a result of an amount or concentration of nutrients such as glucose, ions, or vitamins consumed or depleted by an infectious agent 102 such as a bacteria, fungus, or virus.

In one embodiment, the first sample effluent 134A, the second sample effluent 134B, or a combination thereof can comprise hydrogen ions ($H_{3O}$) as a byproduct of bacterial cell metabolism or growth. In other embodiments, the first sample effluent 134A, the second sample effluent 134B, or a combination thereof can comprise adenosine triphosphate (ATP), carbon dioxide ($CO_2$), lactic acid, carbonic acid, nitrates ($NO_3^-$), or a combination thereof produced by or attributed to the infectious agent 102.

In an alternative embodiment shown in FIG. 1, the same EIS sensor 116A can be used to analyze the first sample effluent 134A and the second sample effluent 134B. In this embodiment, the EIS sensor 116A can be cleaned or recalibrated after each analysis or use.

In yet another embodiment, the first EIS sensor 116A, the second EIS sensor 116B, or a combination thereof can be integrated into the first filter 110A, the second filter 110B, or a combination thereof. For example, the first EIS sensor 116A can be integrated into the first filter 110A and the second EIS sensor 116B can be integrated into the second filter 110B.

A parameter analyzer 114 can monitor an electrical characteristic (see FIG. 4) of the first EIS sensor 1161 exposed to the first sample effluent 1341 in step IF. The parameter analyzer 114 can also monitor the electrical characteristic of the second EIS sensor 116B exposed to the second sample effluent 134B in step 1F. In one example embodiment, the parameter analyzer 114 can be an impedance analyzer. In another example embodiment, the parameter analyzer 114 can be a capacitance analyzer. In this embodiment, the electrical characteristic of the first EIS sensor 116A can be referred to as a first electrical characteristic and the electrical characteristic of the second EIS sensor 116B can be referred to as the second electrical characteristic.

When only one EIS sensor 116A is used to sample the sample effluents, the parameter analyzer 114 can monitor the electrical characteristic of the one EIS sensor 116A exposed to the first sample effluent 134A and the parameter analyzer 114 can also monitor the electrical characteristic of the one EIS sensor 116A exposed to the second sample effluent 134B. In this embodiment, the electrical characteristic of the one EIS sensor 116A while sampling the first sample effluent 134A can be referred to as the first electrical characteristic and the electrical characteristic of the one EIS sensor 116A while sampling the second sample effluent 134B can be referred to as the second electrical characteristic.

The electrical characteristic can include an electrical impedance or impedance change, a voltage or voltage change, a current or change in current, a capacitance or a capacitance change, a characteristic change that is affected by a change in capacitance such as a change in a resonant frequency, a resistance or resistance change, a noise level or noise level change, a subthreshold swing, a level of induction or induction change, or a combination thereof measured at or near the first EIS sensor 116A, the second EIS sensor 116B, or a combination thereof.

The parameter analyzer 114 can be electrically or communicatively coupled to the first EIS sensor 116A, the second EIS sensor 116B, or a combination thereof to monitor the electrical characteristic of the first EIS sensor 116A, the second EIS sensor 116B, or a combination thereof over time. The parameter analyzer 114 can also be connected to a display or display component configured to provide a read-out of the electrical characteristic of the first EIS sensor 116A, the second EIS sensor 116B, or a combination thereof. When only one EIS sensor 116A is used to sample the sample effluents, the parameter analyzer 114 can be electrically or communicatively coupled to the one EIS sensor 116A.

In certain embodiments, the parameter analyzer 114 can be a mobile device, a handheld device, a tablet device, or a computing device such as a laptop or desktop computer. The parameter analyzer 114 can compare the first electrical characteristic with the second electrical characteristic to assess the susceptibility of the infectious agent 102 to the anti-infective 104.

The first electrical characteristic can differ from the second electrical characteristic when the solution characteristic 136 of the first sample effluent 134A differs from the solution characteristic 136 of the second sample effluent 134B as a result of differences in the solution temperature, the concentration of solutes present in the sample effluents, or the amount of solutes present in the sample effluents. For example, the first electrical characteristic and the second electrical characteristic can differ when the solution characteristic 136 of the first sample effluent 134A and the solution characteristic of the second sample effluent 134B differ in their pH temperature, the concentration of another ion, or a combination thereof.

The parameter analyzer 114 or a reader communicatively coupled to the parameter analyzer 114 can assess the susceptibility of the infectious agent 102 to the anti-infective 104 as a binary assessment or a gradated or tiered assessment. In one embodiment, the parameter analyzer 114 or a reader communicatively coupled to the parameter analyzer 114 can assess the susceptibility of the infectious agent 102 as either resistant or non-resistant to the anti-infective 104. In this embodiment, the second filter 110B or the second filter surface 126B can comprise a set amount of the anti-infective 104. The parameter analyzer 114 or a reader communicatively coupled to the parameter analyzer 114 can then assess the susceptibility of the infectious agent 102 as either resistant or non-resistant based on any detected differences in first electrical characteristic and the second electrical characteristic.

The parameter analyzer 114 or a reader communicatively coupled to the parameter analyzer 114 can assess the susceptibility of the infectious agent 102 as not resistant to the anti-infective 104 when the parameter analyzer 114 or a reader communicatively coupled to the parameter analyzer 114 fails to detect a difference or a statistically significant difference between the first electrical characteristic and the second electrical characteristic. More specifically, a statistically significant difference in the electrical characteristic can be a difference exceeding a threshold value.

In other embodiments, the parameter analyzer 114 or a reader communicatively coupled to the parameter analyzer 114 can assess the level of susceptibility of the infectious agent 102 on a gradated For example, the parameter analyzer 114 or a reader communicatively coupled to the parameter analyzer 114 can assess the susceptibility of the infectious agent 102 as being resistant, mildly susceptible, or susceptible to the anti-infective 104. In these embodiments, additional filter surfaces, including the second filter surface 126B and a third filter surface, can be used which comprise anti-infectives 104 of different concentrations. While three categories of susceptibility are discussed, it should be understood by one of ordinary skill in the art that four or greater categories of susceptibility or four or greater filters can be used to assess the level of susceptibility of the infectious agent 102 to differing concentrations of the anti-infective 104.

The steps depicted in FIG. 1 do not require the particular order shown to achieve the desired result and certain steps or processes may occur in parallel.

FIG. 2A illustrates a side cross-sectional view of an example EIS sensor 200. The EIS sensor 200 can be any of the first. EIS sensor 116A or the second. EIS sensor 116B. The EIS sensor 200 can have an external reference electrode 202 extending into a fluid sample 204. The fluid sample 204 can be any of the first sample effluent 134A or the second sample effluent 134B. The fluid sample 204 can also contain one or more electrolytes or analytes.

An EIS sensor 200 can comprise an electrolyte or electrically conducting solution, such as the fluid sample 204, an insulator layer 216, and a semiconductor layer 206 which can be connected or coupled to one or more metal contacts 208 or contact layers. As depicted in FIG. 2A, the EIS sensor 200 can comprise the fluid sample 204 acting as the electrolyte, the insulator layer 216, the semiconductor layer 206 the contact layer 208, a substrate layer 210 or a combination thereof. The substrate layer 210 can be composed of, but is not limited to, any non-conducting material such as a polymer, an oxide, a ceramic, or a composite thereof.

The semiconductor layer 206 can be composed of, but is not limited to, silicon or any other semiconducting material which allows a voltage to be applied through the metal contact layer 208, the semiconductor layer 206, the insulator layer 216, and/or the fluid sample 204 or electrolyte to an external reference electrode 202. The semiconductor layer 206 can also be made of an organic semiconductor, a carbon nanotube, graphene, an organic conductor such as those derived from polyacetylene, polyaniline, Quinacridone, Poly(3,4-ethylenedioxythiophene) or PEDOT, PEDOT: polystyrene sulfonate (PSS), or a combination thereof.

The insulator layer 216 (which can also be referred to as an isolator layer) can be a high-k dielectric layer or a material layer having a high dielectric constant. (k). For example, the insulator layer 216 can comprise aluminum oxide, hafnium oxide, titanium oxide, zirconium oxide, yttrium oxide, tantalum oxide, hafnium silicate, zirconium silicate, silicon nitride, aluminum nitride, hafnium nitride, zirconium nitride, or a combination thereof. As a more specific example, the insulator layer 216 can comprise aluminum dioxide, hafnium dioxide, zirconium dioxide, or a combination thereof. In other embodiments, the insulator layer 216 can comprise a silicon dioxide layer.

As depicted in FIG. 2A, the semiconductor layer 206 can be disposed or placed on a contact layer 208. The contact layer 208 can be composed of, but is not limited to, a metal.

For example, the contact layer 208 can be a gold layer, an aluminum layer, a platinum layer, or a composite thereof. The contact layer 208 can be disposed or placed on the substrate layer 210.

As depicted in FIG. 2A, the fluid sample 204, the insulator layer 216, the semiconductor layer 206, and the contact layer 208 can be surrounded by a container wall 214. The container wall 214 can be made of an inert or non-conductive material. The container wall 214 can hold or delivery the fluid sample 204 or electrolyte to the EIS sensor 200.

As depicted in FIG. 2A, the EIS sensor 200 can also comprise an external reference electrode 202 in liquid communication with the fluid sample 204. The external reference electrode 202 can be used to apply a known potential to the EIS sensor 200. The external reference electrode 202 can have a stable and well-mown internal voltage and can act as a differential noise filter for removing electrical noise from measurements taken by the sensor. The system can use the external reference electrode to determine or record a relative change in the electrical characteristic of the sensor rather than having to ascertain an absolute change. The system can also use the external reference electrode to determine or record a relative difference between the electrical characteristic of the sensors. In one embodiment, the external reference electrode 202 can be a standalone probe or electrode. In other embodiments, the external reference electrode 202 can be coupled to the parameter analyzer 114 or a reader connected to the parameter analyzer 114. The parameter analyzer 114 can also be used to apply a voltage to the external reference electrode 202.

In one embodiment, the external reference electrode 202 can be a silver/silver chloride (Ag/AgCl) electrode. In other embodiments, the external reference electrode 202 can be a saturated calomel reference electrode (SCE) or a. copper-copper (II) sulfate electrode (CSE). In another embodiment not shown in FIG. 2A, a quasi or pseudo reference electrode, such as a metal/metal electrode, a salt/chloride electrode, or a combination thereof can be placed on the substrate layer 210. In yet another embodiment, this quasi or pseudo electrode can be covered by an additional functionalization layer or passivation layer such as a KCL electrolyte gel.

In one or more embodiments, the operation of the EIS sensor 200 can involve the parameter analyzer 114 (or other voltage source) applying a DC polarization voltage (usually in the range of +/−5V) to the metal contact layer 208 and the external reference electrode 202 via the semiconductor layer 206. the insulator layer 216, a functionalization layer (if any), and the fluid sample 204 or electrolyte to set a working point. Next, the parameter analyzer 114 can apply a small superimposed AC voltage (usually in the 10-50 mV range or the Hz-kHz range) to the EIS sensor 200 in order to measure the capacitance or another electrical characteristic, such as a resonant frequency, or response of the EIS sensor 200 using the parameter analyzer 114. The capacitance is a function of the applied DC voltage applied to the EIS sensor 200 and an interfacial potential at the electrolyte/insulator interface or the electrolyte/functionalization layer interface. An example capacitance/voltage (C/V) measurement curve is provided in FIG. 4. Depending on the concentration or amount of an analyte, ion, or cellular byproduct present in the fluid sample 204 or electrolyte, a horizontal shift ($\Delta V$) of the C/V measurement curve will occur when such voltages are applied to the same fluid sample 204 or electrolyte solution over time or different fluid samples or different electrolyte. solutions. This potential horizontal shift ($\Delta V$) of the C/V measurement curve can be evaluated at a fixed capacitance value within the linear region of the C/V measurement curve. The capacitance can be fixed by using a feedback circuit which can allow an analyzer or reader to directly measure or calculate the potential horizontal shift ($\Delta V$) of the C/V measurement curve.

The capacitance is a function of the applied DC voltage applied to the EIS structure and interfacial potential at the electrolyte/insulator or electrolyte/functionalization layer. A typical C/V measurement curve is provided in FIG. 4. Due to the electrochemical interaction ($\Delta V$), a horizontal shift of the C/V curve is visible, depending on the analyte concentration in the solution. As a resulting measuring signal the potential shift can be evaluated at a fixed capacitance value within the linear region of the C/V curve. The measured capacitance can be fixed by using a feedback circuit, allowing to directly measuring potential shifts.

FIG. 2B illustrates a side cross-sectional view of another embodiment of the EIS sensor 200. In this embodiment, the EIS sensor 200 can include a functionalization layer 218 placed or disposed on the insulator layer 216. The functionalization layer 218 can comprise silanes, DNA, proteins, antibodies, self-assembled mono layers (SAMs) buffered hydrogels, PVC, parylene, polyACE, or any other biochemically active materials.

Figure 3A:
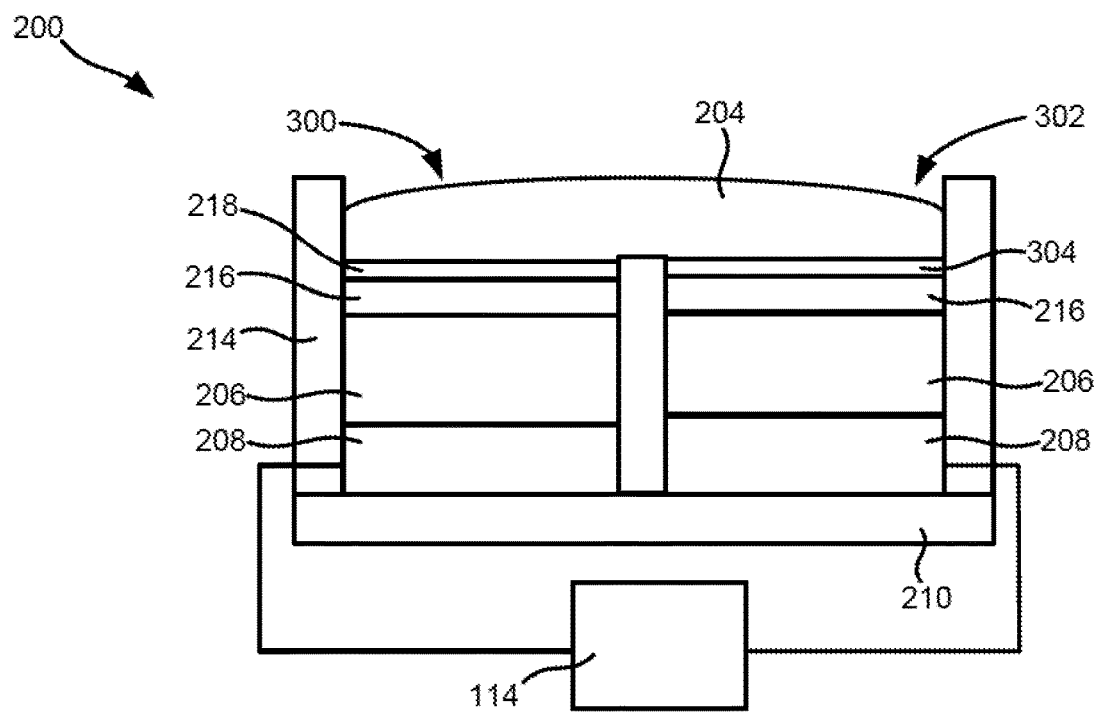
FIG. 3A illustrates a side view of another embodiment of an EIS sensor.

FIG. 3A illustrates a side cross-sectional view of another embodiment of the EIS sensor 200. As depicted in FIG. 3A, the EIS sensor 200 can have a dual sensor assembly including a first sensor assembly 300 and a second sensor assembly 302. In this embodiment, the first sensor assembly 300 and the second sensor assembly 302 can be disposed or placed on the same substrate 210. In addition, the fluid sample 204 can flow over or be exposed to both the first sensor assembly 300 and the second sensor assembly 302 simultaneously. In this embodiment, the first sensor assembly 300 and the second sensor assembly 302 can be separated by a container wall 214 or container divide. The first sensor assembly 300 can comprise a functionalization layer 218 disposed on or covering the insulator layer 216. The second sensor assembly 302 can act as an on-chip reference electrode.

As shown in FIG. 3A, a passivation layer 304 can be disposed on or cover the insulator layer 216 of the second sensor assembly 302. The passivation layer 304 can be configured to prevent the second sensor assembly 302 from interacting with the analyte, ions, or other byproducts in the fluid sample 204 or electrolyte solution. For example, the passivation layer 304 can be a pH-insensitive layer. The passivation layer 304 can comprise silanes, self-assembled monolayers (SAMs), buffered hydrogels, parylene, polyACE, or any other biochemically inert material.

In one embodiment, the first sensor assembly 300 can include an insulator layer 216 disposed on or covering a semiconductor layer 206. In this embodiment, the semiconductor layer 206 of the first sensor assembly 300 can be disposed on or cover a contact layer 208. Moreover, the contact layer 208 of the first sensor assembly 300 can be disposed on or cover the substrate layer 210. Also, in this embodiment, the second sensor assembly 302 can include a passivation layer 304 disposed on or covering the insulator layer 216. In addition, the insulator layer 216 can be disposed on or cover the semiconductor layer 206. Furthermore, in this embodiment, the semiconductor layer 206 of the second sensor assembly 302 can be disposed on or cover the contact layer 208. Moreover, the contact layer 208 of the second sensor assembly 302 can be disposed on or cover the substrate layer 210 and can be separated from the contact layer 208 of the first sensor assembly 300 by the container wall 214 or a container divide.

In this embodiment, the parameter analyzer 114 can have a lead connection wire, such as a copper wire, connected to the contact layer 208 of the first sensor assembly 300 and another lead connection wire connected to the contact layer 208 of the second sensor assembly 302.

In this and other embodiments, the EIS sensor 200 shown in FIG. 3A miniaturizes the sensor set-up shown in FIGS. 2A and 2B. The second sensor assembly 302 can act as an on-chip reference electrode and obviates the need of an external reference electrode, such as the external reference electrode 202. The passivation layer 304 of the second sensor assembly 302 prevents the interaction of the second sensor assembly 302 with the ions, analyte, or other byproducts in the fluid sample 204 or electrolyte solution in order to be able to differentiate the electrical signals obtained by the parameter analyzer 114 or another reader.

Figure 3B:
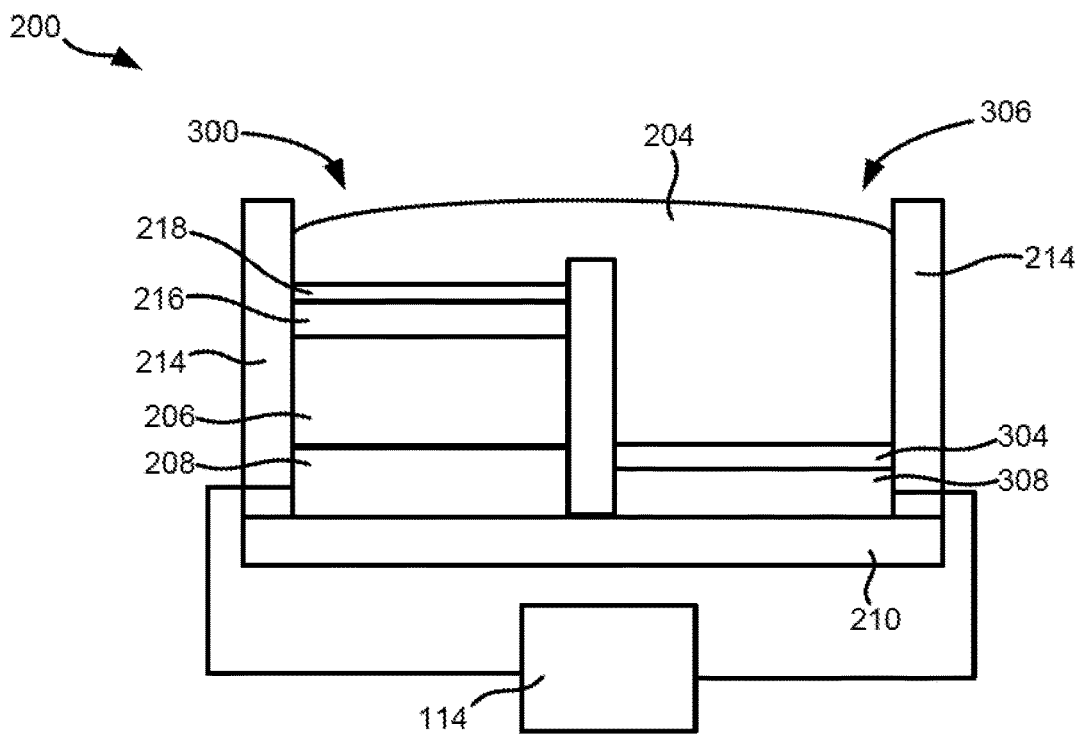
FIG. 3B illustrates a side view of yet another embodiment of an EIS sensor.

FIG. 3B illustrates a side cross-sectional view of yet another embodiment of the EIS sensor 200. As depicted in FIG. 3B, the EIS sensor 200 can have the first sensor assembly 300 of FIG. 3A and an on-chip reference electrode 306 made of a conductor layer 308. In one embodiment, the conductor layer 308 can be a metal covered with a metal salt such as a metal chloride. For example, the conductor layer 308 can be a silver/silver chloride contact. In this embodiment, the conductor layer 308 can be covered by a passivation layer 304 such as a KCL electrolyte gel, to prevent interference with the analyte, ions, or byproducts in the fluid sample 204 or electrolyte solution. For example, the passivation layer 304 can be comprised of silanes, SAMs buffered hydrogels, PVC, parylene, polyACE, or any other biochemically-inert or pH insensitive material.

Although example EIS sensor 200 are presented in FIGS. 2A, 2B, 3A, and 3B, it is understood by one of ordinary skill in the art that the EIS sensors disclosed in U.S. Pat. No. 5,182,005 to Schwiegk et at; the EIS sensors disclosed in Poghossian et al., Penicillin Detection by Means of Field-Effect Based Sensors: EnFET, Capacitive EIS Sensor or LAPS? *Sensors and Actuators* B (2001) 78: 237; the EIS sensors disclosed in Schoning, Michael J., 'Playing Around' with Field-Effect Sensors on the Basis of EIS Structures, LAPS and ISFETs, *Sensors* (2005) 5: 126-138; and the EIS sensors disclosed in Kumar et al., Sensitivity Enhancement Mechanisms in Textured Dielectric Based Electrolyte-Insulator-Semiconductor (EIS) Sensors, *ECS Journal of Solid State Science and Technology* (2015) 4(3): N18-N23, the contents of which are all incorporated herein by reference in their entireties, can also be used to detect the susceptibility of an infectious agent in a fluid sample to one or more anti-infectives according to the methods or processes disclosed herein. In addition, the EIS sensor 200 can comprise filters, well plates, wells, readers, analyzers, electrodes, sensor contacts, sensor components, sensor layers, or substrates disclosed in any of U.S. patent application Ser. No. 14/297,603, filed on Jun. 5, 2014; U.S. patent application Ser. No. 14/586,802, filed on Dec. 30, 2014; U.S. patent application Ser. No. 14/878,936, filed on Oct. 8. 2015; U.S. patent application Ser. No. 15/081,491, filed on Mar. 25, 2016: U.S. patent application Ser. No. 15/159,625, filed on May 19, 2016; U.S. patent application Ser. No. 15/236,260 filed on Aug. 12, 2016; and U.S. Pat. No. 9,377,456, the contents of which are all hereby incorporated by reference in their entireties.

Figure 4:
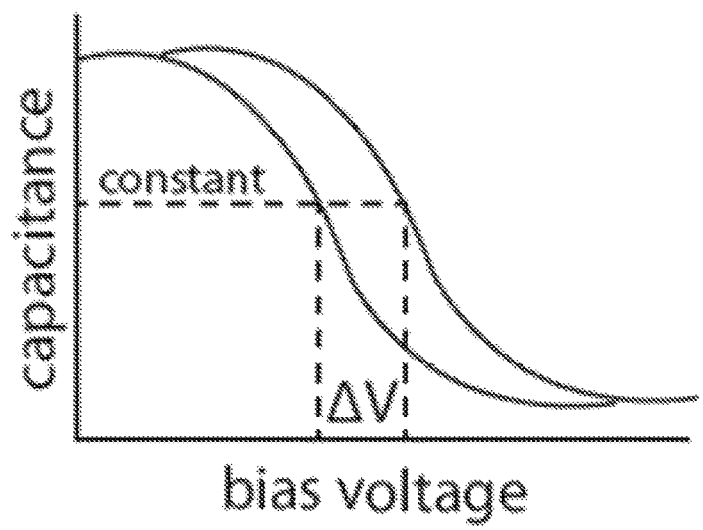
FIG. 4 illustrates example readouts from an analyzer or reader of the system.

FIG. 4 illustrates one example of capacitance/voltage (C/V) curves displayed by the system 100. As can be seen in the C/V curves of FIG. 4, the difference between the solution characteristics of two fluid samples or one fluid sample over time can be measured by the change in the voltage ($\Delta V$) at a constant capacitance. In one example, the hydroxyl groups of insulator layer 216 can interact with the hydrogen ions ($H^+$) in the fluid sample 204 or electrolyte solution. This can create an additional voltage or capacitance at the surface of the EIS sensor 200. This additional voltage/capacitance will alter the C/V curves. Also, for example, the analyte or ion can interact with the functionalization layer 218 causing the same effect. To obtain a dynamic sensor response, the EIS sensor 200 can also be operated in a constant capacitance mode. In this constant capacitance mode, the capacitance can be set a fixed value (e.g., a flat-band capacitance) and the voltage shift ($\Delta V$) that results from the surface, potential generated at the interface of the electrolyte/insulator or electrolyte/functionalization layer can be directly recorded.

Figure 5:
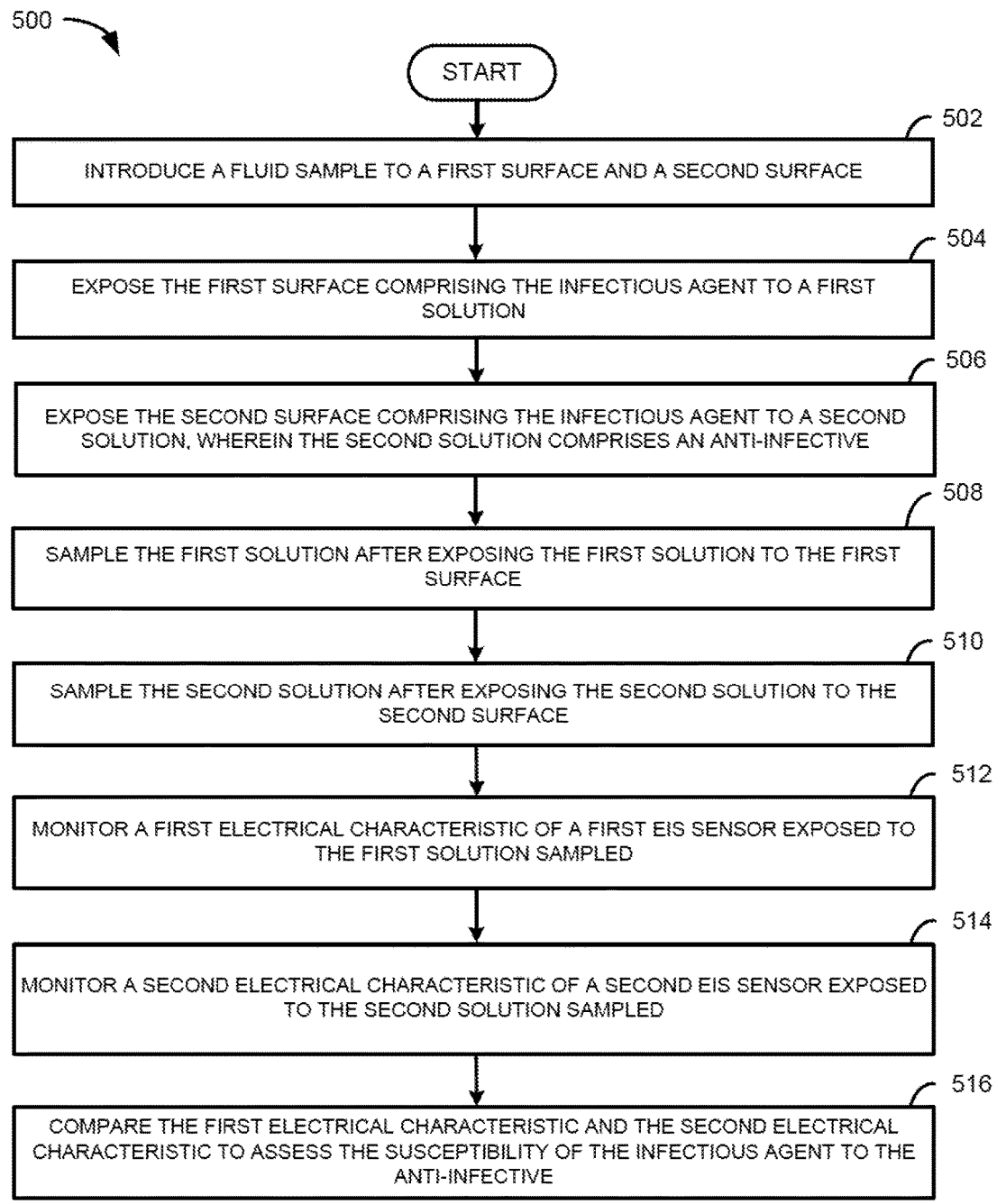
FIG. 5 illustrates an embodiment of a method for detecting a susceptibility of an infectious agent to one or more anti-infectives.

FIG. 5 illustrates a method 500 for detecting a susceptibility of an infectious agent 102 to one or more anti-infectives 104. The method 500 can include introducing a fluid sample 124 to a first surface, such as the first filter surface 126A, and a second surface, such as the second filter surface 126B, in, a step 502. The method 500 can also include exposing the first surface to a first solution, such as the nutrient solution 130, in a step 504. The first surface can comprise the infectious agent 102 when the infectious agent 102 is present in the fluid sample 124.

The method 500 can also include exposing the second surface to a second solution, such as additional instances of the nutrient solution 130 in a step 506. The second surface can comprise one or more anti-infectives 104 or anti-infectives of differing concentrations. The second surface can also comprise the infectious agent 102 when the infectious agent 102 is present in the fluid sample 124.

The method 500 can also include sampling the first solution after exposing the first solution to the first surface in step 508. Sampling the first solution can include sampling the effluent or outflow of the first solution, such as the first sample effluent 134A. In one embodiment, sampling the first solution can also involve separating the first solution from the first surface so the first solution is not in fluid communication with the first surface, the infectious agent 102 on the first surface, or a combination thereof when sampled. The method 500 can also include sampling the second solution after exposing the second solution to the second surface in step 510. Sampling the second solution can include sampling the effluent or outflow of the second solution, such as the second sample effluent 134B. In one embodiment, sampling the second solution can also involve separating the second solution from the second surface so the second solution is not in fluid communication with the second surface, the infectious agent 102 on the second surface, or a combination thereof when sampled.

The method 500 can also include monitoring a first electrical characteristic of a first EIS sensor 116A exposed to the first solution sampled in step 512. The method 500 can also include monitoring a second electrical characteristic of a second EIS sensor 116B exposed to the second solution sampled in step 514. The method 500 can further include comparing the first electrical characteristic and the second electrical characteristic to assess the susceptibility of the infectious agent 102 to the anti-infective 104 in step 516.

The flowcharts or process flows depicted in FIG. 5 do not require the particular order shown to achieve the desired result and certain steps or processes may occur in parallel.

Figure 6:
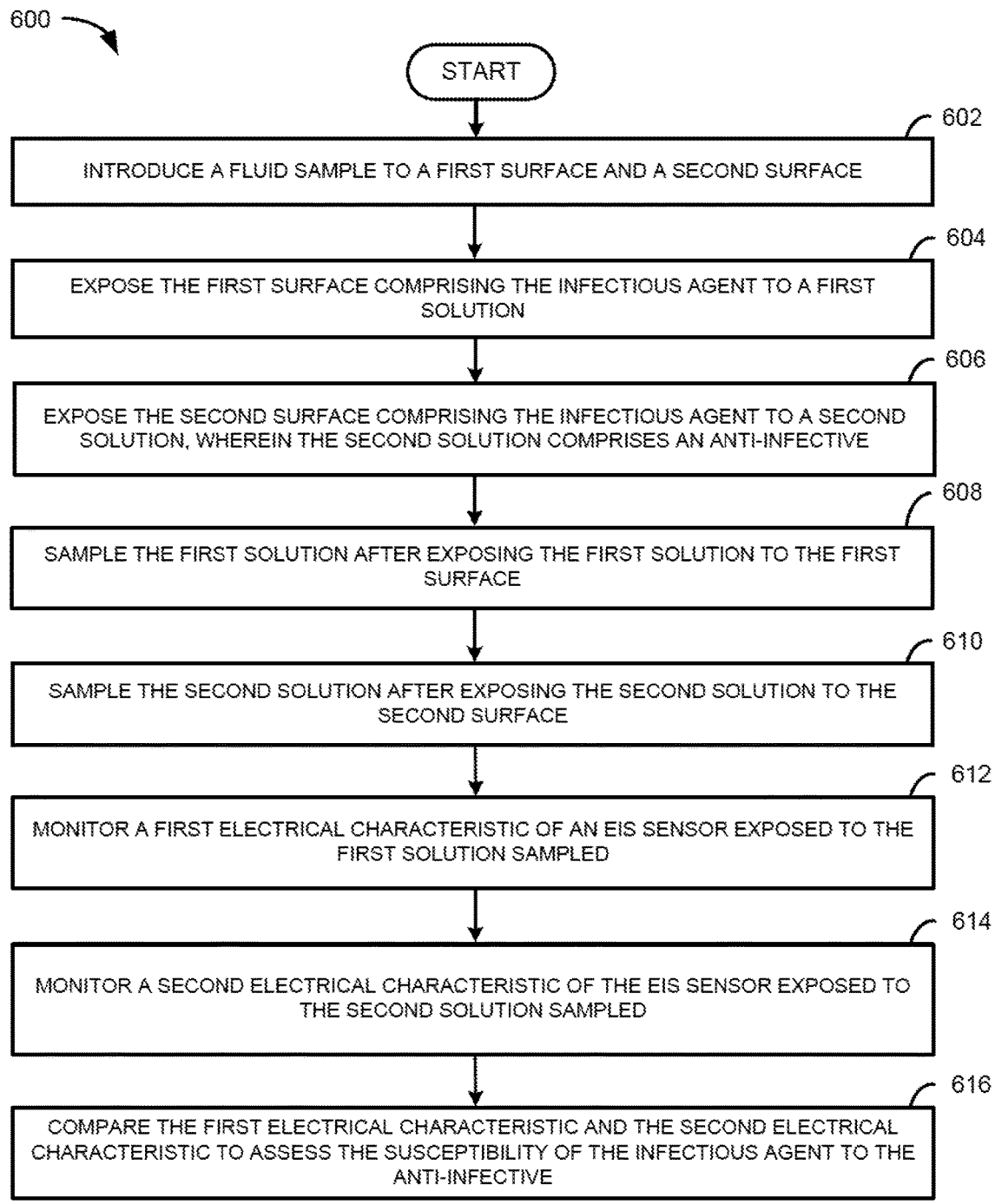
FIG. 6 illustrates another embodiment of the method for detecting a susceptibility of an infectious agent to one or more anti-infectives.

FIG. 6 illustrates another method 600 for detecting a susceptibility of an infectious agent 102 to one or more anti-infectives 104. The method 600 can include introducing a fluid sample 124 to a first surface, such as the first filter surface 126A, and a second surface, such as the second filter surface 126B, in a step 602. The method 600 can also include exposing the first surface to a first solution, such as the nutrient solution 130, in a step 604. The first surface can comprise the infectious agent 102 when the infectious agent 102 is present in the fluid sample 124.

The method 600 can also include exposing the second surface to a second solution, such as additional instances of the nutrient solution 130 in a step 606. The second surface can comprise one or more anti-infectives 104 or anti-infectives of differing concentrations. The second surface can also comprise the infectious agent 102 when the infectious agent 102 is present in the fluid sample 124.

The method 600 can also include sampling the first solution after exposing the first solution to the first surface in step 608. Sampling the first solution can include sampling the effluent or outflow of the first solution, such as the first sample effluent 134A. In one embodiment, sampling the first solution can also involve separating the first solution from the first surface so the first solution is not in fluid communication with the first surface, the infectious agent 102 on the first surface, or a combination thereof. The method 600 can also include sampling the second solution after exposing the second solution to the second surface in step 610. Sampling the second solution can include sampling the effluent or outflow of the second solution, such as the second sample effluent 134B. In one embodiment, sampling the second solution can also involve separating the second solution from the second surface so the second solution is not in fluid communication with the second surface, the infectious agent 102 on the second surface, or a combination thereof.

The method 600 can also include monitoring a first electrical characteristic of an EIS sensor 116 exposed to the first solution sampled in step 612. The method 600 can also include monitoring a second electrical characteristic of the EIS sensor 116 exposed to the second solution sampled in step 614. The method 600 can further include comparing the first electrical characteristic and the second electrical characteristic to assess the susceptibility of the infectious agent 102 to the anti-infective 104 in step 616.

The flowcharts or process flows depicted in. FIG. 6 do not require the particular order shown to achieve the desired result and certain steps or processes may occur in parallel.

Each of the individual variations or embodiments described and illustrated herein has discrete components and features which may be readily separated from or combined with the features of any of the other variations or embodiments. Modifications may be made to adapt a particular situation, material, composition of matter, process, process act(s) or step(s) to the objective(s), spirit or scope of the present invention.

Methods recited herein may be carried out in any order of the recited events that is logically possible, as well as the recited order of events. For example, the flowcharts or process flows depicted in the figures do not require the particular order shown to achieve the desired result. Moreover, additional steps or operations may be provided or steps or operations may be eliminated to achieve the desired result.

It will be understood by one of ordinary skill in the art that all or a portion of the methods disclosed herein may be embodied in a non-transitory machine readable or accessible medium comprising instructions readable or executable by a processor or processing unit of a computing device or other type of machine.

Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

This disclosure is not intended to be limited to the scope of the particular forms set forth, but is intended to cover alternatives, modifications, and equivalents of the variations or embodiments described herein. Further, the scope of the disclosure fully encompasses other variations or embodiments that may become obvious to those skilled in the art in view of this disclosure. The scope of the present invention is limited only by the appended claims.

What is claimed is:

1. A method for detecting a susceptibility of an infectious agent to an anti-infective, the method comprising:
   introducing a fluid sample to a first surface and a second surface;
   exposing the first surface comprising the infectious agent to a. first solution;
   exposing the second surface comprising the infectious agent to a second solution, wherein at least one of the second surface and the second solution comprises an anti-infective:
   sampling the first solution after exposing the first solution to the first surface;
   sampling the second solution after exposing the second solution to the second surface;
   monitoring a first electrical characteristic of a first electrolyte-insulator-semiconductor (EIS) sensor exposed to the first solution sampled;
   monitoring a second electrical characteristic of a second EIS sensor exposed to the second solution sampled; and
   comparing, the first electrical characteristic and the second electrical characteristic to assess the susceptibility of the infectious agent to the anti-infective.

2. The method of claim 1, wherein the first surface is a filter surface or a well surface.

3. The method of claim 2, wherein the second surface is separate from the first surface and is another instance of the filter surface or the well surface.

4. The method of claim 1, wherein at least one of the first surface and the second surface is a non-clogging filter.

5. The method of claim 1, wherein at least one of the first surface and the second surface comprises pores of sequentially smaller pore size.

6. The method of claim 1, wherein comparing the first electrical characteristic and the second electrical characteristic includes determining a difference between the first electrical characteristic and the second electrical characteristic and wherein the difference between the first electrical characteristic and the second electrical characteristic is a result of a difference in a solution characteristic of the first solution and the second solution.

7. The method of claim wherein the difference in the solution characteristic of the first solution and the second solution is a difference in at least one of a molecular count, a concentration of an ion, and a solution temperature.

8. The method of claim 1. wherein the infectious agent s a bacteria, a fungus, a virus, or a prion.

9. The method of claim 1, wherein the first EIS sensor and the second EIS sensor are housed by a protective chamber and the protective chamber is at least one of an electrically isolated environment, a temperature controlled chamber, and a light controlled chamber.

10. The method of claim 1. further comprising directing the first solution to the first surface or directing the second solution to the second surface using a pump.

11. A method for detecting a susceptibility of an infectious agent to an anti-infective, the method comprising:
introducing a fluid sample to a first surface and a second surface;
exposing the first surface comprising the infectious agent to a first solution;
exposing the second surface comprising the infectious agent to a second solution, wherein at least one of the second surface and the second solution comprises an anti-infective;
sampling the first solution from the first surface after exposing the first surface to the first solution;
sampling the second solution from the second surface after exposing the second surface to the second solution;
monitoring a first electrical characteristic of an electrolyte-insulator-semiconductor (EIS) sensor exposed to the first solution sampled;
monitoring a second electrical characteristic of the EIS sensor exposed to the second solution sampled; and
comparing the first electrical characteristic and the second electrical characteristic to assess the susceptibility of the infectious agent to the anti-infective.

12. The method of claim 11, wherein the first surface is a filter surface or a well surface.

13. The method of claim 12, wherein the second surface is separate from the first surface and is another instance of the filter surface or the well surface.

14. The method of claim 11, wherein at least one of the first surface and the second surface is a non-clogging filter.

15. The method of claim 11, wherein at least one of the first surface and the second surface comprises pores of sequentially smaller pore size.

16. The method of claim 11, wherein comparing the first electrical characteristic and the second electrical characteristic includes determining a difference between the first electrical characteristic and the second electrical characteristic and wherein the difference between the first electrical characteristic and the second electrical characteristic is a result of a difference in a solution characteristic of the first solution and the second solution.

17. The method of claim 16, wherein the difference in the solution characteristic of the first solution and the second solution is a difference in at least one of a molecular count, a concentration of an ion, and a solution temperature.

18. The method of claim 11, wherein the infectious agent is a bacteria, a fungus, a virus, or a prion.

19. The method of claim 11. wherein the EIS sensor is housed by a protective chamber and the protective chamber is at least one of an electrically isolated environment, a temperature controlled chamber, and a light controlled chamber.

20. The method of claim 11, further comprising directing the first solution to the first surface or directing the second solution to the second surface using a pump.

* * * * *